United States Patent [19]

Cecchi et al.

[11] Patent Number: 5,719,308
[45] Date of Patent: Feb. 17, 1998

[54] ENZYMATIC PROCESS FOR THE PREPARATION OF OPTICALLY ACTIVE TETRALIN DERIVATIVES

[75] Inventors: Roberto Cecchi; Laura Barzaghi; Umberto Guzzi, all of Milan, Italy

[73] Assignee: Sanofi, Paris, France

[21] Appl. No.: 685,488

[22] Filed: Jul. 24, 1996

Related U.S. Application Data

[62] Division of Ser. No. 425,743, Apr. 20, 1995, Pat. No. 5,573,949.

[30] Foreign Application Priority Data

Apr. 21, 1994 [EP] European Pat. Off. ............. 94400863

[51] Int. Cl.$^6$ ................................................ C07C 69/76
[52] U.S. Cl. ................................................ 560/56
[58] Field of Search ................................... 560/56

[56] References Cited

PUBLICATIONS

Chem. Abstracts 105:172006 (1986).
Chem Abstracts 98:125571 (1982).

*Primary Examiner*—Paul J. Killos
*Attorney, Agent, or Firm*—Bacon & Thomas

[57] ABSTRACT

The present invention relates to an enzymatic process for the preparation of optically active tetrahydro-2-naphthoic acids from the corresponding racemic esters by reaction with a lipase.

4 Claims, No Drawings

ENZYMATIC PROCESS FOR THE PREPARATION OF OPTICALLY ACTIVE TETRALIN DERIVATIVES

This application is a division of application Ser. No. 08/425,743, filed Apr. 20, 1995, now U.S. Pat. No. 5,573,949.

The present invention relates to a process for the preparation of optically active tetralin derivatives.

The application of enzymes to enantioselective synthesis has been extensively studied over the last ten years (Klibanov, Acc. Chem. Res., 23: 114, 1990). More particularly, the enzyme lipase has been used in asymmetric esterifications and transesterifications, especially in the preparation of alcohols, esters and acids.

Numerous derivatives of tetralin structure in optically active form are described in the literature, especially as synthesis intermediates (EP-A-436435, EP-B-347313, EP-A-211721, DE 2803582, EP-A-334538) or as laboratory tools in pharmacological and biochemical assays. For example, 8-hydroxy-2-diisopropylaminotetralin (8-OH-DPAT) and its (R) and (S) enantiomers are used as reference products in tests on serotonin, especially as $5HT_{1A}$ agonists (J. Med. Chem., 1989, 32: 779–783; Eur. J. Med. Chem., 1991, 26: 215–220).

More particularly, EP-A-436435 describes methoxy-substituted 1,2,3,4-tetrahydro-2-naphthoic acids in optically active form. The separation of the enantiomers of these acids from the racemate, when effected by the usual chemical methods, is not only laborious but also rather inefficient and the results, in terms of enantiomeric purity of the separated products, are sometimes less than satisfactory.

It has now been found that the enantiomers can be resolved by a very simple and efficient reaction based on the kinetics of an enzymatic hydrolysis of alkyl tetralincarboxylates.

In particular, it has been found that by subjecting a methoxy-substituted 1,2,3,4-tetrahydro-2-naphthoic acid ester to the action of lipase, the enzyme hydrolyzes the (R) form of the ester preferentially and leaves the (S) form virtually untouched, thereby making it possible to separate the two forms.

The present invention therefore relates to a process for the preparation of the compounds of formula (I) in optically active form:

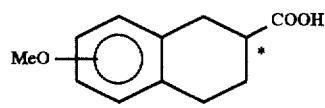

wherein:

(a) a racemic ester of the formula

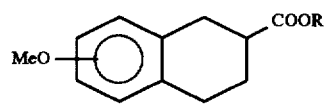

in which R is a $C_1-C_3$-alkyl, is hydrolyzed with a lipase; then (b) when about 50% of the ester has been hydrolyzed to the acid, the hydrolysis is interrupted by inactivation of the enzyme and the unreacted ester of (S) configuration of the formula

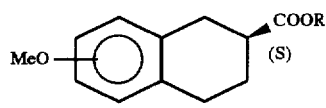

is recovered; and finally (c) either said ester of formula (II') is hydrolyzed and the acid of (S) configuration of the formula

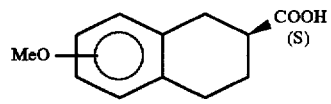

is isolated, or the acid of (R) configuration of the formula

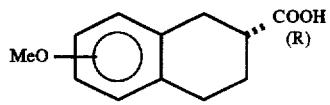

as obtained from the lipase hydrolysis reaction is isolated after interruption of the hydrolysis in step (b).

In formulae (I), (II), (I'), (I") and (II') above and in the description below, Me is the methyl group.

The esters of formula (II) are described for example in EP-A-300404, EP-A-436435, Synthesis, 9: 727–9 (1983), and J. Am. Chem. Soc., 104: 7609–22 (1982), or alternatively they can easily be prepared by esterification of the corresponding racemic acids. Of these starting materials, those of formula (II) in which R is methyl or ethyl are particularly preferred.

The lipase used in the reaction of step (a) is porcine pancreatic lipase (PPL), which is an enzyme sold commercially in the fresh or lyophilized form (the lipase used is preferably porcine pancreatic lipase—Type II, Sigma L-3126). The lipase enzyme can optionally be immobilized by covalent bonding to a polymer matrix, for example a resin, according to the techniques described for example by S. Fukuy, Enzymes Eng., 6:191–200 (1982).

The enantioselective hydrolysis reaction of step (a) is preferably carried out in an aqueous medium, mixed with a water-miscible organic solvent and in the presence of a buffer system. More particularly, the reaction medium is buffered with a buffer at a pH of about 7, prepared by known methods, for example phosphate buffer. This pH corresponds to the pH of the enzyme's optimal performance characteristics.

The reaction temperature of step (a) can be chosen freely within a temperature range in which the enzyme is not deactivated; this is generally between 0° C. and 60° C., advantageously between 5° C. and 40° C., preferably between 10° and 30° C. and normally room temperature.

The organic solvent used in step (a) of the process of the invention is a water-miscible solvent, for example an alcohol such as methanol, ethanol, n-propanol, iso-propanol, n-butanol, sec-butanol, iso-butanol or tert-butanol, a ketone such as acetone, or a cyclic ether such as tetrahydrofuran or dioxane, tert-butanol being a particularly advantageous solvent. The amount of said solvent is not a critical parameter; in general, the amount of solvent used is sufficient to dissolve the starting ester.

Normally the racemic ester of formula (II) is dissolved in a water-miscible organic solvent and the solution obtained is added to a buffer at pH 7. The enzyme PPL, which catalyzes the selective hydrolysis of the (R) enantiomer of the ester, is then added to this mixture. The reaction is controlled by the addition of a base, especially NaOH, in order to keep the pH almost constant at a value of about 7. The reaction is terminated when the enzyme has hydrolyzed half of the ester, especially the (R) isomer of the ester, i.e. after the addition of an amount of base equal to at most half the mol equivalents of the starting ester.

To stop the reaction in step (b), the enzyme is inactivated, for example by the addition of a base so as to increase the pH of the solution to a basic value, preferably of at least about 8. The base used can be inorganic, such as an alkali metal hydroxide, especially sodium or potassium hydroxide, or an alkali metal carbonate, especially sodium or potassium carbonate, or it can be an amine, preferably a tertiary amine such as triethylamine.

The isomer of (S) configuration of the ester of formula (II'), which has not been hydrolyzed by the lipase, is extracted into a water-immiscible organic solvent and isolated by the usual techniques, for example by evaporation of the solvent under reduced pressure.

The residual aqueous phase contains the free acid corresponding to the starting ester of (R) absolute configuration of formula (II).

The two enantiomers, (S) and (R), are separated in step (c).

To isolate the (S) isomer of formula (I'), the methyl ester (II') is hydrolyzed under acid or basic conditions. Hydrolysis under basic conditions corresponds to a saponification carried out by the usual techniques, for example with an alkali metal hydroxide such as sodium or potassium hydroxide. The acid (I') is isolated according to the conventional techniques by acidification with a mineral or organic acid, for example with hydrochloric or sulfuric acid. Hydrolysis under acid conditions is carried out with an acid such as hydrochloric or sulfuric acid and the (S) enantiomer of formula (I') is isolated by neutralization with a base such as sodium hydroxide.

To obtain the (R) enantiomer of formula (I"), said acid, which constitutes the lipase hydrolysis product of step (a) and which remains in the aqueous phase after separation of the ester (II'), is recovered and isolated by the conventional methods, especially by acidification of the aqueous solution and filtration of the precipitate formed.

If it is desired to obtain the derivatives (I") of (R) absolute configuration, it is advantageous to stop the reaction of step (a) just before 50% of the ester has been hydrolyzed, i.e. before all the (R) isomer of the ester has reacted. This makes it possible to obtain the pure (R) acid of formula (I") before the secondary hydrolysis reaction of the (S) isomer of the ester of formula (II) intervenes.

If, on the other hand, it is desired to obtain the derivatives of (S) absolute configuration, the hydrolysis should be continued slightly beyond the consumption of 50% of the ester (II) so as to be sure that all the (R) isomer has been hydrolyzed by the enzyme and that all the residual ester therefore has the (S) configuration.

Thus, according to a preferred feature of the present invention, the enzymatic hydrolysis in step (b) is interrupted just before 50% of the compound (II) has been hydrolyzed, by the addition of sodium hydroxide to basic pH, the unreacted compound (II') is extracted into a water-immiscible organic solvent, the organic phase is then discarded and, in step (c), the aqueous phase is treated with a mineral or organic acid and the acid of (R) configuration of formula (I") precipitated in this way is separated off.

Thus, according to a preferred feature of the present invention, the enzymatic hydrolysis in step (b) is interrupted just after 50% of the compound (II) has been hydrolyzed, by the addition of sodium hydroxide to basic pH, the unreacted compound (II') is extracted into a water-immiscible organic solvent, the aqueous phase is then discarded, the ester (II') is isolated and, in step (c), said ester of formula (II') is hydrolyzed and the acid of (S) configuration of formula (I') is isolated.

The (R) and (S) isomeric acids are obtained in optically pure form by the process of the present invention, the enantiomeric excesses being well above 90%.

The esters (II'), which can be isolated in extremely pure form, are novel products and form a further subject of the present invention. Of these compounds, those of formula (II') in which R is methyl are particularly preferred. Among the last mentioned compounds those for which MeO is in 6- or 7-position are advantageous.

The enantiomeric acids of formula (I) in which the methoxy group is in the 8-position of the tetrahydronaphthalene are novel compounds which are useful as intermediates in the synthesis of optically active 8-OH-DPAT.

Their absolute configuration was determined by conversion of the acid assumed to be the (R) isomer, obtained directly by the above enzymatic hydrolysis, to the corresponding optically active 8-methoxy-2-(N-benzyl)amino-1, 2,3,4-tetrahydronaphthalene derivative by a stereochemistry-preserving reaction; 8-methoxy-(2R)-2-(N-benzyl)amino-1,2,3,4-tetrahydronaphthalene is described in Acta Chem. Scand. B, 1988, 42: 231, and the (R) configuration of said acid could be confirmed by comparing the optical rotations.

According to a further feature, the present invention therefore relates to the (R) and (S) enantiomers of 8-methoxy-1,2,3,4-tetrahydro-2-naphthoic acid.

The compounds of formulae (I') and (I") are very versatile reaction intermediates which are useful in the synthesis of numerous derivatives of tetralin structure.

More particularly, the compounds of formulae (I') and (I") are described as intermediates in the syntheses of the optically active amines of formula (III):

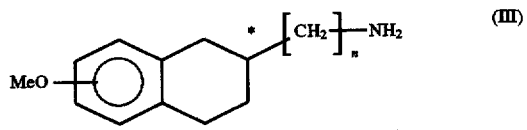

in which n is 0 or 1 and the asterisk (*) denotes the chiral carbon atom in its (R) or (S) form.

The process for the preparation of the amines of formula (III) above comprises carrying out enzymatic hydrolysis kinetics on the racemic ester of formula (II):

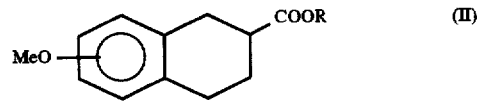

in which R is as defined above, with the aid of porcine pancreatic lipase by the method described in steps (a), (b) and (c) above, and then converting the resulting isomeric acids of formulae (I') and (I") to amines of formula (III) by the methods described in EP-A-436435, especially by the Curtius reaction directly on the optically active acid in the case of the compounds of formula (III) in which n=0, and by reduction of the amide obtained from the optically active acid in the case of the compounds in which n=1.

Thus, according to another feature, the present invention relates to a process for the preparation of an optically active amine of formula (III) above in which n is 0 or 1 and the asterisk (*) denotes the chiral carbon atom in its (R) or (S) form, and its salts, wherein (a) a racemic ester of the formula

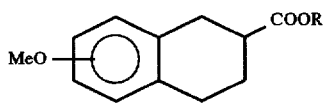

in which R is a $C_1$-$C_3$-alkyl, is hydrolyzed with a lipase; then (b) when about 50% of the ester has been hydrolyzed to the acid, the hydrolysis is interrupted by inactivation of the enzyme and the unreacted ester of (S) configuration of the formula

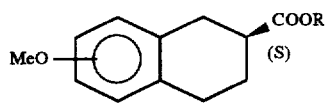

is recovered; then (c) either said ester of formula (II') is hydrolyzed and the acid of (S) configuration of the formula

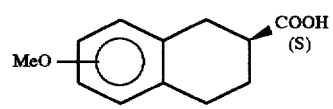

is isolated,
or the acid of (R) configuration of the formula

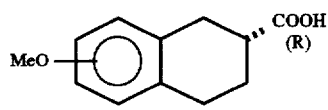

as obtained from the lipase hydrolysis reaction is isolated after interruption of the hydrolysis in step (b); and finally (d) either the isomeric acids are reacted with an azide by the Curtius reaction in order to isolate an amine of formula (III) in which n is 0, or the isomeric acids (I') and (I") or the ester (II') are converted to the corresponding amide and the latter is reduced in order to isolate an amine of formula (III) in which n is 1, said amines being isolated in the form of the free base or one of their acid addition salts, or converted to one of their acid addition salts.

The Curtius reaction of step (d) can be either of the conventional type, involving formation of the azide, its decomposition to the isocyanate and hydrolysis of the latter to the amine, or of the modified type, involving the use of diphenylphosphoryl azide in the presence of tert-butanol and hydrolysis of the tert-butoxycarbonylamino intermediate to the amine, according to the techniques described in the literature.

The stereochemical configuration of the asymmetric carbon atom is preserved during these reactions.

Obviously, if it is desired to obtain the amines of formula (III) of (S) absolute configuration, the starting acid used will be that of formula (I') or its ester (II'); if it is desired to obtain the amines of formula (III) of (R) absolute configuration, the acid of formula (I") will be used as the starting material.

The Examples which follow illustrate the invention more clearly.

The enantiomeric excesses (ee) were calculated on the basis of the HPLC data, the analysis of which is performed under the following conditions:

(a) Column: CHIRALCEL OD mobile phase: hexane/trifluoroacetic acid mixture=100/1

λ 280 nm

Retention time (min):

flow rate: 1.0 ml/min 6-methoxy-1,2,3,4-tetrahydro-(2R)-2-naphthoic acid= 20.3

6-methoxy-1,2,3,4-tetrahydro-(2S)-2-naphthoic acid= 23.5

Retention time (min):

flow rate: 1.5 ml/min 7-methoxy-1,2,3,4-tetrahydro-(2R)-2-naphthoic acid= 19.2

7-methoxy-1,2,3,4-tetrahydro-(2S)-2-naphthoic acid=16.8

(b) Column: CHIRALCEL OD mobile phase: hexane/isopropanol mixture=100/2 flow rate: 0.5 ml/min

λ 280 nm

Retention time (min):

methyl 7-methoxy-1,2,3,4-tetrahydro-(2R)-2-naphthoate=19.5 methyl 7-methoxy-1,2,3,4-tetrahydro-(2S)-2-naphthoate= 22.6

(c) Column: CHIRALCEL OD mobile phase: hexane/isopropanol mixture=85/5 flow rate: 1 ml/min

λ 280 nm

Retention time (min):

6-methoxy-1,2,3,4-tetrahydronaphthalene-(2R)-2-carboxamide=8.96

(d) Column: CHIRALCEL OD mobile phase: hexane/isopropanol/trifluoroacetic acid mixture=95/5/1 flow rate: 1.3 ml/min

λ 280 nm

Retention time (min):

8-methoxy-1,2,3,4-tetrahydronaphthalene-(2S)-2-naphthoic acid=19.6 methyl 8-methoxy-1,2,3,4-tetrahydronaphthalene-(2S)-2-naphthoate=19.2

8-methoxy-1,2,3,4-tetrahydronaphthalene-(2R)-2-naphthoic acid=10.7 methyl 8-methoxy-1,2,3,4-tetrahydronaphthalene-(2R)-2-naphthoate=7.8

(e) Column: CHIRALCEL OD mobile phase: hexane/isopropanol/trifluoroacetic acid mixture=95/5/1 flow rate: 0.5 ml/min

λ 280 nm

Retention time (min):

methyl 6-methoxy-1,2,3,4-tetrahydro-(2R)-2-naphthoate=12.95 methyl 6-methoxy-1,2,3,4-tetrahydro-(2S)-2-naphthoate= 14.3

5-methoxy-1,2,3,4-tetrahydronaphthalene-(2S)-2-naphthoic acid=19.3 methyl 5-methoxy-1,2,3,4-tetrahydronaphthalene-(2S)-2-naphthoate=13.9

5-methoxy-1,2,3,4-tetrahydronaphthalene-(2R)-2-naphthoic acid=16.7 methyl 5-methoxy-1,2,3,4-tetrahydronaphthalene-(2R)-2-naphthoate=12.5

The formula for calculating the enantiomeric excesses is as follows:

$$ee = \frac{A1 - A2}{A1 + A2}$$

in which A1 and A2 represent the areas corresponding to the two isomers, (R) and (S), obtained by HPLC analysis.

The buffer solution used in the following Examples is a phosphate buffer marketed by Merck under the code Merck 9439.

EXAMPLE 1

6-Methoxy-1,2,3,4-tetrahydro-(2R)-2-naphthoic acid 3 g (0.0136 mol) of methyl 6-methoxy-1,2,3,4-tetrahydro-2-naphthoate are dissolved in 100 ml of tert-butanol, and 300 ml of phosphate buffer at pH 7 are added to the solution prepared in this way. The pH of the solution, which rises to 7.3–7.5, is lowered to 7.1 by the addition of 1N HCl. 1.5 g of Sigma PPL enzyme (known as porcine pancreatic lipase type II, crude, Sigma L-3126—50 U/mg using triacetin) are added to the mixture. The pH tends to drop as the reaction progresses, but is kept constant by the addition of a 0.25N solution of NaOH, the pH being controlled by an automatic titration apparatus. After 4–5 hours, when about 22 ml of 0.25N NaOH have been consumed, sodium bicarbonate is added to the solution until the pH is 8 in order to stop the reaction by inactivation of the enzyme. Extraction is carried out with ethyl ether and the two phases are separated. The organic phase contains the unreacted ester principally of (S) configuration, which can be recovered as indicated in Example 2 below. The aqueous phase is acidified with concentrated sulfuric acid and the precipitate formed is filtered off to give 1.16 g of the title acid, which is crystallized from ethyl acetate. M.p. 130°–131° C.; $[\alpha]_D^{20}$=+57.8° (c=1.4%, CHCl$_3$); ee 93.7% (HPLC performed under conditions (a)). This product is purer than that described in EP-A-436435, preparation (O) (i).

Two other preparations carried out under the same conditions gave the same product with ee values of 92% and 93.1% (HPLC performed under conditions (a)).

EXAMPLE 2

6-Methoxy-1,2,3,4-tetrahydro-(2S)-2-naphthoic acid

The residual organic phase from Example 1 is dried over sodium sulfate and evaporated under reduced pressure and the ester (b.p.=128°–132° C. at 0.1 mbar) containing principally the (S) isomer (ee 68.9%, HPLC performed under conditions (a)) is then distilled. 5 g (0.022 mol) of the ester recovered in this way are dissolved in 175 ml of tert-butanol; 500 ml of phosphate buffer at pH 7 are added to the resulting solution. The pH is lowered to 7.04 by the addition of 5% sulfuric acid, and 2.5 g of Sigma PPL (known as porcine pancreatic lipase type II, crude, Sigma L-3126—39 U/mg using triacetin) are added. The pH drops as the reaction progresses; it is kept constant by the addition of a 0.25N solution of NaOH using an automatic titration apparatus. When 12.5 ml of 0.25N NaOH have been consumed, sodium bicarbonate is added until the pH is 8, extraction is carried out with ethyl ether, the two phases are then separated, the aqueous phase containing the recoverable 6-methoxy-1,2,3,4-tetrahydro-(2R)-2-naphthoic acid is discarded, the organic phase is dried over sodium sulfate and the solvent is evaporated off under reduced pressure to give 4.73 g of methyl 6-methoxy-1,2,3,4-tetrahydro-(2S)-2-naphthoate (ee 92%—HPLC performed under conditions (e)). The (S) isomer of the ester obtained in this way is treated with a solution of NaOH and acidified with 1N hydrochloric acid to give 3.2 g of the title acid, which is crystallized from ethyl acetate. M.p. 130°–131° C.; ee 93%, HPLC performed under conditions (a). This product is purer than that described in EP-A-436435, preparation (Q) (i).

Another preparation carried out under the same conditions gave the title product with an ee of 96.6%; $[\alpha]_D^{20}$=−62.2° (c=1.4%, CHCl$_3$).

EXAMPLE 3

6-Methoxy-1,2,3,4-tetrahydro-(2S)-2-naphthoic acid

The method described in Example 1 is followed using 4 g (0.018 mol) of starting ester instead of 3 g, the enzymatic reaction being stopped when 37 ml of 0.25N NaOH have been consumed and sodium bicarbonate being added until the pH is 8. Extraction is then carried out with ethyl ether, the two phases are separated, the organic phase is dried over sodium sulfate and the solvent is evaporated off under reduced pressure to give 1.85 g of methyl 6-methoxy-1,2,3,4-tetrahydro-(2S)-2-naphthoate (ee 92%, HPLC performed under conditions (e)). The (S) isomer of the ester obtained in this way is treated with a solution of NaOH and acidified with 1N hydrochloric acid to give 1.6 g of the title acid, which is crystallized from ethyl acetate. M.p. 129°–130° C.; $[\alpha]_D^{20}$=−57.3° (c=1.4%, CHCl$_3$); ee 93.0% (HPLC performed under conditions (a)).

EXAMPLE 4

7-Methoxy-1,2,3,4-tetrahydro-(2R)-2-naphthoic acid 5 g (0.022 mol) of methyl 7-methoxy-1,2,3,4-tetrahydro-2-naphthoate are dissolved in 175 ml of tert-butanol, and 500 ml of phosphate buffer at pH 7 are added to the solution prepared in this way. The pH of the solution, which rises to a value of 7.3–7.5, is lowered to 7.1 by the addition of 1N HCl. 3.5 g of Sigma PPL enzyme (known as porcine pancreatic lipase type II, crude, Sigma L-3126—39 U/mg using triacetin) are added to the mixture. The pH tends to drop as the reaction progresses, but is kept constant by the addition of a 0.25N solution of NaOH. After 6 hours, when about 31.75 ml of 0.25N NaOH have been consumed, sodium bicarbonate is added to the solution until the pH is about 8 in order to stop the reaction by inactivation of the enzyme. Extraction is carried out with ethyl ether and the two phases are separated. The organic phase contains the unreacted ester principally of (S) configuration, which can be recovered as indicated in Example 5. The aqueous phase is acidified with concentrated sulfuric acid and the precipitate formed is filtered off to give 1.25 g of the title acid. $[\alpha]_D^{20}$=+43.67° (c=1.4%, CHCl$_3$); ee 93.27% (HPLC performed under conditions (a)). This product is equivalent to that described in preparation (G) (i) of EP-A-436435, obtained after 10 crystallizations.

Two other preparations carried out under the same conditions gave the same product with ee values of 91.65% and 93.52% (HPLC performed under conditions (a)).

EXAMPLE 5

7-Methoxy-1,2,3,4-tetrahydro-(2S)-2-naphthoic acid

The residual organic phase from Example 4 is dried over sodium sulfate and evaporated under reduced pressure to give 3.39 g of the ester containing principally the (S) isomer (ee 37.6%—HPLC performed under conditions (b)), which is distilled (b.p.=130°–135° C. at 0.1 mbar). 3 g (0.014 mol) of the ester recovered in this way are dissolved in 100 ml of tert-butanol; 300 ml of phosphate buffer at pH 7 are added to the resulting solution. The pH is lowered to 7.04 by the addition of 5% sulfuric acid, and 2 g of Sigma PPL (known as porcine pancreatic lipase type II, crude, Sigma L-3126—

39 U/mg using triacetin) are added. The pH drops as the reaction progresses; it is kept constant by the addition of a 0.25N solution of NaOH. After about 6 hours, when 15 ml of 0.25N NaOH have been consumed, sodium bicarbonate is added until the pH is 8, extraction is carried out with ethyl ether, the two phases are then separated, the aqueous phase containing the recoverable 7-methoxy-1,2,3,4-tetrahydro-(2R)-2-naphthoic acid is discarded, the organic phase is dried over sodium sulfate and the solvent is evaporated off under reduced pressure to give 1.5 g of methyl 7-methoxy-1,2,3,4-tetrahydro-(2S)-2-naphthoate (ee 92.3%—HPLC performed under conditions (b)). The (S) isomer of the ester obtained in this way is treated with a solution of NaOH and acidified with 1N hydrochloric acid to give 1.1 g of the title acid. ee 92.3%. This product is equivalent to that described in EP-A-436435, obtained after 10 crystallizations.

Two other preparations carried out under the same conditions gave the title product with the following characteristics:

ee 91.6%; $[\alpha]_D^{20}$=−44.6° (c=1.4%, CHCl$_3$);

ee 93%; $[\alpha]_D^{20}$=−44.3° (c=1.4%, CHCl$_3$).

EXAMPLE 6

7-Methoxy-1,2,3,4-tetrahydro-(2R)-2-naphthaleneamine hydrochloride

A solution of 2 ml (0.0140 mol) of triethylamine in 20 ml of acetone and then 1.6 ml (0.0161 mol) of ethyl chloroformate in 20 ml of acetone are added slowly at a temperature of −10° C. to −5° C. to a solution of 2.5 g (0.0120 mol) of 7-methoxy-1,2,3,4-tetrahydro-(2R)-2-naphthoic acid in 30 ml of acetone. The mixture is stirred at −5° C. for 2 hours and a solution of 1.3 g (0.0193 mol) of NaN$_3$ in 10 ml of water is then added dropwise. After 1 hour at −5° C., the mixture is poured into 200 ml of water and extracted with toluene. The two phases are separated, the organic phase is dried over sodium sulfate and filtered and the solution is heated at 100° C. for 1.5 hours. The solvent is evaporated off under reduced pressure, the residue is taken up with 22 ml of water and 26 ml of 37% hydrochloric acid and the mixture is refluxed for 3.5 hours. After cooling, the pH of the solution is rendered basic by the addition of 3.5N NaOH, extraction is carried out with ethyl ether, the organic phase is dried over sodium sulfate and the solvent is evaporated off under reduced pressure. The hydrochloride of the base obtained in this way is prepared with a saturated solution of hydrochloric acid in ethyl ether. This gives 1.6 g of the title compound, which is crystallized from isopropanol to give 1.2 g of product. M.p. 205° C.—207° C.; $[\alpha]_D^{20}$=+66.6° (c=0.5%, MeOH).

EXAMPLE 7

7-Methoxy-1,2,3,4-tetrahydro-(2S)-2-naphthaleneamine hydrochloride

The method of Example 6 is followed using 2.5 g of 7-methoxy-1,2,3,4-tetrahydro-(2S)-2-naphthoic acid as the starting material. This gives 1 g of the title compound. M.p. 205° C.-207° C.; $[\alpha]_D^{20}$=−66.4° (c=0.4%, MeOH).

EXAMPLE 8

(2R)-2-Aminomethyl-6-methoxy-1,2,3,4-tetrahydronaphthalene hydrochloride (i) 6-Methoxy-1,2,3,4-tetrahydronaphthalene-(2R)-2-carboxamide 3.48 ml (0.038 mol) of oxalyl chloride and a few drops of dimethylformamide are added dropwise to a solution of 7.01 g (0.034 mol) of 6-methoxy-1,2,3,4-tetrahydro-(2R)-2-naphthoic acid in 150 ml of methylene chloride under anhydrous conditions. The mixture is stirred at room temperature for 5 hours and then added dropwise to a solution of 21.52 ml (0.102 mol) of hexamethyldisilazane in 15 ml of anhydrous methylene chloride. The mixture is stirred at room temperature overnight. 25 ml of methanol are added and the mixture is stirred for 30 minutes. It is poured into 200 ml of 5% sulfuric acid and extracted with methylene chloride. The two phases are separated, the organic phase is washed with a saturated solution of ammonium chloride and dried over sodium sulfate and the solvent is evaporated off under reduced pressure to give 11.8 g of product, which is purified by flash chromatography using a methylene chloride/methanol mixture=9/1 as the eluent. This gives 4.64 g of 6-methoxy-1,2,3,4-tetrahydronaphthalene-(2R)-2-carboxamide. ee 94.5% (HPLC performed under conditions (c)); $[\alpha]_D^{20}$=+52.9° (c=1.4%, CHCl$_3$).

(ii) (2R)-2-Aminomethyl-6-methoxy-1,2,3,4-tetrahydronaphthalene hydrochloride

The compound obtained in step (i) above is subjected to the reaction described in EP-A-436435, preparation (O) (iii). This gives (2R)-2-aminomethyl-6-methoxy-1,2,3,4-tetrahydronaphthalene hydrochloride. M.p. 255°–256° C.; $[\alpha]_D^{20}$=+75.3° (c=1.4%, CHCl$_3$).

EXAMPLE 9

8-Methoxy-1,2,3,4-tetrahydro-(2R)-2-naphthoic acid 0.743 g (0.0034 mol) of methyl 8-methoxy-1,2,3,4-tetrahydro-2-naphthoate is dissolved in 26 ml of tert-butanol, and 75 ml of phosphate buffer at pH 7 are added to the solution prepared in this way. The pH of the solution, which rises to 7.3–7.5, is lowered to 7.1 by the addition of 1N HCl. 0.836 g of Sigma PPL enzyme (known as porcine pancreatic lipase type II, crude, Sigma L-3126—46 U/mg using triacetin) is added to the mixture. The pH tends to drop as the reaction progresses, but is kept constant by the addition of a 0.25N solution of NaOH, the pH being controlled by an automatic titration apparatus. After 6.5 hours, the mixture is poured into a 5% solution of sodium bicarbonate in order to stop the reaction by inactivation of the enzyme. Extraction is carried out with ethyl ether and the two phases are separated. The organic phase contains the unreacted ester principally of (S) configuration, which can be recovered as indicated in Example 10 below. The aqueous phase is acidified with 10% sulfuric acid and extracted with chloroform; the organic phase is filtered on Célite and dried over sodium sulfate and the solvent is evaporated off under reduced pressure to give 0.303 g of the title acid, which is crystallized from isopropyl ether. ee 95.2% (HPLC performed under conditions (d)); m.p. 137°–138° C.; $[\alpha]_D^{25}$= +54.6° (c=1.4%, CH$_3$OH).

EXAMPLE 10

8-Methoxy-1,2,3,4-tetrahydro-(2S)-2-naphthoic acid

The residual organic phase from Example 9 is dried over sodium sulfate and evaporated off under reduced pressure to give 0.403 g of methyl 8-methoxy-1,2,3,4-tetrahydro-(2S)-2-naphthoate (ee 90.4%—HPLC performed under conditions (d)). The (S) isomer of the ester directly obtained in this way is treated with a solution of 10 ml of methanol and 4 ml of 1N NaOH. The mixture is refluxed for 2 hours, the solution is concentrated and the residue is taken up with a saturated aqueous solution of NaCl and washed with ethyl ether. The aqueous phase is acidified to pH 1 by the addition of 5% sulfuric acid and extracted with methylene chloride, the extract is dried over sodium sulfate and the solvent is evaporated off under reduced pressure to give 0.39 g of the title product, which is purified by chromatography on a silica gel column using a $CH_2Cl_2/MeOH$ mixture=95/5 as the eluent. The product is subsequently purified by crystallization from 10 ml of ethanol. M.p. 140.5° C.; $[\alpha]_D^{25}$=−50.5° (c=1.4%, $CHCl_3$); ee=90.0% (HPLC performed under conditions (d)).

Another preparation carried out under the same conditions gave the title product with an ee of 94.8%.

The absolute configuration of the title acid was demonstrated, as described in Example 13 below, by conversion of said acid to 8-methoxy-2-(N-benzyl)amino-1,2,3,4-tetrahydronaphthalene, whose (S) absolute configuration is known.

EXAMPLE 11

5-Methoxy-1,2,3,4-tetrahydro-(2R)-2-naphthoic acid 0.8 g (0.0036 mol) of methyl 5-methoxy-1,2,3,4-tetrahydro-2-naphthoate is dissolved in 28 ml of tert-butanol, and 80 ml of phosphate buffer at pH 7 are added to the solution prepared in this way. The pH of the solution, which rises to 7.3–7.5, is lowered to 7.1 by the addition of dilute $H_2SO_4$. 0.450 g of Sigma PPL enzyme (known as porcine pancreatic lipase type II, crude, Sigma L-3126—46 U/mg using triacetin) is added to the mixture. The pH tends to drop as the reaction progresses, but is kept constant by the addition of a 0.25N solution of NaOH, the pH being controlled by an automatic titration apparatus. After 8 hours, sodium bicarbonate is added to the solution until the pH is 7.7 in order to stop the reaction by inactivation of the enzyme. Extraction is carried out with isopropyl ether and the two phases are separated. The organic phase contains the unreacted ester principally of (S) configuration. The aqueous phase is acidified with concentrated sulfuric acid and extracted with ethyl ether, the organic phase is dried over sodium sulfate and the solvent is evaporated off under reduced pressure. The product obtained is crystallized from isopropyl ether to give 0.12 g of the title compound. M.p. 150°–152° C.; $[\alpha]_D^{20}$=+55.9° (c=1.4%, $CHCl_3$); ee 85.6% (HPLC performed under conditions (e)).

Another preparation carried out according to the same procedure gave the title product with an ee of 83%.

EXAMPLE 12

5-Methoxy-1,2,3,4-tetrahydro-(2S)-2-naphthoic acid

The method described in Example 11 is followed using 0.74 g of racemic starting ester instead of 0.8 g, 26 ml of tert-butanol, 75 ml of phosphate buffer and 0.83 g of Sigma PPL enzyme (known as "porcine pancreatic lipase" type II, Crude, Sigma L-3126—36 U/mg using triacetin). When 8 ml of 0.25N NaOH have been consumed, the reaction is stopped by the addition of sodium bicarbonate until the pH is 8. Extraction is carried out with ethyl ether, the two phases are separated, the organic phase is dried over sodium sulfate and the solvent is evaporated off under reduced pressure to give 0.37 g of methyl 5-methoxy-1,2,3,4-tetrahydro-(2S)-2-naphthoate with an ee of 60%. This product is treated with 3 ml of methanol and 3 ml of a 2N aqueous solution of NaOH and the mixture is stirred at room temperature for 4 hours. It is diluted with water and washed with ethyl ether. The aqueous phase is acidified with concentrated hydrochloric acid and extracted with ethyl acetate. The organic phase is washed with water and dried over sodium sulfate and the solvent is evaporated off under reduced pressure to give the title compound, which is crystallized from 5 ml of isopropyl ether. M.p. 150°–152° C.; $[\alpha]_D^{20}$=−49.6° (c=1.4%, $CHCl_3$); ee 58.9% (HPLC performed under conditions (e)).

EXAMPLE 13

8-Methoxy-(2R)-2-(N-benzyl)amino-1,2,3,4-tetrahydronaphthalene hydrochloride (i) 8-Methoxy-(2R)-2-(N-tert-butoxycarbonyl)amino-1,2,3,4-tetrahydronaphtalene 0.23 ml (1.65 mmol) of triethylamine and 0.35 ml (1.65 mmol) of diphenylphosphoryl azide (DPPA) are added to a mixture of 0.3 g (1.5 mmol) of 8-methoxy-1,2,3,4-tetrahydro-(2R)-2-naphthoic acid and 7 ml of tert-butyl alcohol under nitrogen. The mixture is refluxed for 20 hours, poured into 20 ml of a 5% aqueous solution of sodium bicarbonate and extracted with chloroform and the organic phase is washed with a 3% solution of phosphoric acid and then with a 1N solution of NaOH. The organic phase is dried over sodium sulfate and the solvent is evaporated off under reduced pressure to give 0.38 g of a white solid, which is directly subjected to the reaction of step (ii).

(ii) 8-Methoxy-(2R)-2-(N-benzyl-N-tert-butoxycarbonyl)-amino-1,2,3,4-tetrahydronaphtalene 0.2 g (0.72 mmol) of the product obtained in step (i) in 1.5 ml of tetrahydrofuran is added to a suspension of 0.021 g (0.72 mmol) of 80% NaH in 3 ml of tetrahydrofuran under nitrogen. The mixture is heated at 60° C. for 10 minutes, 0.086 g (0.72 mmol) of benzyl bromide is added and the mixture is stirred at 60° C. for 8 hours. It is poured into 20 ml of a 5% aqueous solution of sodium bicarbonate and extracted with ethyl ether, the organic phase is dried over sodium sulfate and the solvent is evaporated off under reduced pressure. The residue is purified by chromatography on a silica gel column using an ethyl acetate/hexane mixture=1/4 as the eluent to give 0.1 g of the title compound, which is subjected to the reaction of step (iii).

(iii) 8-Methoxy-(2R)-2-(N-benzyl)amino-1,2,3,4-tetrahydronaphtalene hydrochloride 0.1 g of the compound obtained in the previous step is dissolved in 3 ml of trifluoroacetic acid and the solution is stirred at room temperature for 12 hours. The solvent is evaporated off, the residue is taken up with methanol and the solvent is evaporated off to dryness. This operation is repeated 3 times. The oil obtained is treated with a saturated solution of hydrochloric acid in methanol and the solvent is evaporated off under reduced pressure to give the title compound, which is crystallized from a methanol/isopropyl ether mixture. M.p. 237°–238° C.; $[\alpha]_D^{25}$=+59.2° (c=1%, $CH_3OH$); ee 93% (reference: Acta Chem. Scand. B, 1988, 42: 231).

EXAMPLE 14

8-Methoxy-(2R)-2-amino-1,2,3,4-tetrahydronaphthalene hydrochloride (i) 8-Methoxy-1,2,3,4-tetrahydro-(2R)-2-naphthoic acid 1.1 g (0.0051 mol) of methyl 8-methoxy-1,2,3,4-tetrahydro-2-naphthoate are dissolved in 39 ml of tert-butanol, and 112 ml of phosphate buffer at pH 7 are added to the solution prepared in this way. The pH of the solution, which rises to 7.3–7.5, is lowered to 7.1 by the addition of 1N HCl. 1.25 g of Sigma PPL enzyme (known as porcine pancreatic lipase type II, crude, Sigma L-3126—46 U/mg using triacetin) are added to the mixture. The pH tends to drop as the reaction progresses, but is kept constant by the addition of a 0.25N solution of NaOH, the pH being controlled by an automatic titration apparatus. After 7 hours, the mixture is poured into a 5% solution of sodium bicarbonate in order to stop the reaction by inactivation of the enzyme. Extraction is carried out with ethyl ether and the two phases are separated. The organic phase contains the unreacted ester principally of (S) configuration, which can be recovered. The aqueous phase is acidified with 10% sulfuric acid and extracted with chloroform; the organic phase is filtered on Celite and dried over sodium sulfate and the solvent is evaporated off under reduced pressure to give 0.42 g of the title acid. ee 98% (HPLC performed under conditions (d)).

(ii) 8-Methoxy-(2R)-2-(N-tert-butoxycarbonyl)amino-1,2,3,4-tetrahydronaphthalene 0.3 ml (2.2 mmol) of triethylamine and 0.46 ml (2.2 mmol) of diphenylphosphoryl azide (DPPA) are added to a mixture of 0.4 g (2 mmol) of the acid obtained in the previous step and 9.4 ml of tert-butyl alcohol under nitrogen. The mixture is refluxed for 20 hours, poured into 26 ml of a 5% aqueous solution of sodium bicarbonate and extracted with chloroform and the organic phase is washed with a 3% solution of phosphoric acid and then with a 1N solution of NaOH. The organic phase is dried over sodium sulfate and the solvent is evaporated off under reduced pressure to give 0.52 g of a white solid, which is directly subjected to the following reaction of step (iii).

(iii) 8-Methoxy-(2R)-2-amino-1,2,3,4-tetrahydronaphthalene hydrochloride

A mixture of 0.17 g (0.61 mmol) of the product obtained in the previous step and 7 ml of trifluoroacetic acid is stirred at room temperature for 12 hours. The solvent is evaporated off under reduced pressure, the residue is taken up with methanol and the solvent is evaporated off under reduced pressure. This operation is repeated 3 times. The residue is treated with a saturated solution of hydrochloric acid in methanol and the solvent is evaporated off. The residue is crystallized from a methanol/ethyl ether mixture to give the title compound. M.p. 244° C. dec.; $[\alpha]_D^{25}$=+51.2° (c=1%, CH$_3$OH); ee=94%.

EXAMPLE 15

8-Methoxy-(2S)-2-amino-1,2,3,4-tetrahydronaphthalene hydrochloride 0.3 g of the title compound is obtained by following the procedure described in Example 14, except that 0.26 g of 8-methoxy-1,2,3,4-tetrahydro-(2S)-2-naphthoic acid is used as the starting material. M.p. 242°–244° C. dec.; $[\alpha]_D^{25}$=−48.5° (c=1%, CH$_3$OH); ee=89.2%.

EXAMPLE 16

(2R)-2-Aminomethyl-6-methoxy-1,2,3,4-tetrahydronaphthalene hydrochloride (i) 6-Methoxy-1,2,3,4-tetrahydro-(2R)-2-naphthoic acid 5 g of methyl 6-methoxy-1,2,3,4-tetrahydro-2-naphthoate are dissolved in 170 ml of tert-butanol, and 500 ml of phosphate buffer at pH 7 are added to the solution prepared in this way. The pH of the solution, which rises to 7.3–7.5, is lowered to 7.1 by the addition of 1N HCl. 2.5 g of Sigma PPL enzyme (known as porcine pancreatic lipase type II, crude, Sigma L-3126—50 U/mg using triacetin) are added to the mixture. The pH tends to drop as the reaction progresses, but is kept constant by the addition of a 0.25N solution of NaOH, the pH being controlled by an automatic titration apparatus. After 5 hours, sodium bicarbonate is added to the solution until the pH is about 8 in order to stop the reaction by inactivation of the enzyme. Extraction is carried out with ethyl ether and the two phases are separated. The organic phase contains the unreacted ester principally of (S) configuration, which can be recovered. The aqueous phase is acidified with concentrated sulfuric acid and the precipitate formed is filtered off to give 1.8 g of the title acid, which is crystallized from ethyl acetate. ee 93%.

(ii) 6-Methoxy-1,2,3,4-tetrahydronaphthalene-(2R)-2-carboxamide 0.9 ml (9.7 mmol) of oxalyl chloride and a few drops of dimethylformamide are added dropwise to a solution of 1.8 g (8.7 mmol) of 6-methoxy-1,2,3,4-tetrahydro-(2R)-2-naphthoic acid in 39 ml of methylene chloride under anhydrous conditions. The mixture is stirred at room temperature for 5 hours and then added dropwise to a solution of 5.5 ml (26 mmol) of hexamethyldisilazane in 4 ml of anhydrous methylene chloride. The mixture is stirred at room temperature overnight. 6 ml of methanol are added and the mixture is stirred for 30 minutes. It is poured into 50 ml of 5% sulfuric acid and extracted with methylene chloride. The two phases are separated, the organic phase is washed with a saturated solution of ammonium chloride and dried over sodium sulfate and the solvent is evaporated off under reduced pressure. The crude product is purified by flash chromatography using a methylene chloride/methanol mixture=9/1 as the eluent to give 1.5 g of 6-methoxy-1,2,3,4-tetrahydronaphthalene-(2R)-2-carboxamide. ee 95%.

(iii) (2R)-2-Aminomethyl-6-methoxy-1,2,3,4-tetrahydronaphthalene hydrochloride

The compound obtained in step (ii) above is subjected to the reaction described in EP-A-436435, preparation (O) (iii). This gives (2R)-2-aminomethyl-6-methoxy-1,2,3,4-tetrahydronaphthalene hydrochloride. M.p. 255°–256° C.; $[\alpha]_D^{20}$=+75.3° (c=1.4%, CHCl$_3$).

What is claimed is:

1. A compound of formula (II')

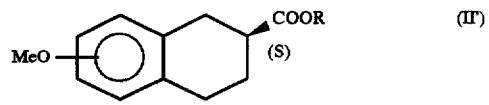

in which R is a $C_1$–$C_3$-alkyl, which compound is in optically pure form in an enantiomeric excess above 90%, provided that the methoxy group is not in position 5 of the naphthalene ring.

2. A compound selected from the group consisting of:
methyl 6-methoxy-1,2,3,4-tetrahydro-(2S)-2-naphthoate;
methyl 7-methoxy-1,2,3,4-tetrahydro-(2S)-2-naphthoate; and
methyl 8-methoxy-1,2,3,4-tetrahydro-(2S)-2-naphthoate, which compound is in optically pure form in an enantiomeric excess above 90%.

3. 8-methoxy-1,2,3,4-tetrahydro-(2R)-2-naphthoic acid in optically pure form in an enantiomeric excess above 90%.

4. 8-methoxy-1,2,3,4-tetrahydro-(2S)-2-naphthoic acid in optically pure form in an enantiomeric excess above 90%.

* * * * *